(12) United States Patent
Murao et al.

(10) Patent No.: US 7,054,789 B2
(45) Date of Patent: May 30, 2006

(54) ABNORMALITY DETERMINATION AND ESTIMATION METHOD FOR PRODUCT OF PLASTIC WORKING, AND AN ABNORMALITY DETERMINATION AND ESTIMATION DEVICE

(75) Inventors: Masuaki Murao, Toyohashi (JP); Yasuhiro Onishi, Moriguchi (JP)

(73) Assignees: DENSO Corporation, Kariya (JP); Yonekura Mfg. Co., Ltd., Osaka (JP)

( * ) Notice: Subject to any disclaimer, the term of this patent is extended or adjusted under 35 U.S.C. 154(b) by 0 days.

(21) Appl. No.: 10/859,482

(22) Filed: Jun. 2, 2004

(65) Prior Publication Data

US 2004/0249611 A1    Dec. 9, 2004

(30) Foreign Application Priority Data

Jun. 2, 2003    (JP) .............................. 2003-157002

(51) Int. Cl.
*G06F 11/30*    (2006.01)
*G06F 15/00*    (2006.01)
*G21C 17/00*    (2006.01)

(52) U.S. Cl. .................................................... 702/185

(58) Field of Classification Search ................ 702/58, 702/185; 73/808; 360/135
See application file for complete search history.

(56) References Cited

U.S. PATENT DOCUMENTS

| | | | | |
|---|---|---|---|---|
| 5,202,810 | A * | 4/1993 | Nakamura et al. .......... | 360/135 |
| 5,214,595 | A * | 5/1993 | Ozawa et al. ................ | 702/58 |
| 5,448,902 | A | 9/1995 | Thoms et al. | |
| 5,594,178 | A * | 1/1997 | Takahashi et al. ............ | 73/808 |

FOREIGN PATENT DOCUMENTS

| | | |
|---|---|---|
| CN | 1084795 | 4/1994 |
| DE | 39 38 854 | 5/1990 |
| DE | 103 08 845 | 9/2003 |
| JP | 9-251007 | 9/1997 |

OTHER PUBLICATIONS

Oppel, F. et al: "Automatische Ueberwachung Des Stanzvorganges Durch Auswertung Prozessbedingten Koerperschalls—Automatic Control of Punch Processes By Using Structure Born Sound", Technisches Messen TM, R. Oldenbourg, Verlag, Munchen, DE, vol. 52, No. 11, 1985, pp. 411-416, document No. XP-001149675.

Eckert W., et al: "Stanzvorgang Zuverlassig Uberwachen Korperschall Auswerten—Prozessstorung Erkennen", Industrie Anzeiger, Leinfelden-Echterdingen, DE, No. 17, 1991, pp. 40-43, document No. XP-000503248.

E. Doege, F. Meiners, T. Meinde, W. Strache, J.W. Jun: "Metal Forming", Sensors In Manufacturing, 2001, pp. 172-202, document No. XP-002298300.

* cited by examiner

*Primary Examiner*—Michael Nghiem
*Assistant Examiner*—Aditya S. Bhat
(74) *Attorney, Agent, or Firm*—Harness, Dickey & Pierce PLC

(57) ABSTRACT

The abnormality determination and estimation device (200a) estimates the presence or absence of an abnormality of the product of plastic working with respect to an elastic wave in processing of a non-defective product, based on a first elastic wave A1 that is an elastic wave generated in a processing step immediately before an upper die comes into contact with a lower die after the beginning of plastic working, a second elastic wave A2 that is an elastic wave generated in a processing step when the upper die comes into contact with the lower die, and a third elastic wave A3 that is an elastic wave generated in a processing step after the upper die comes into contact with the lower die. This makes it possible to improve the precision of abnormality detection and discriminate the abnormalities.

18 Claims, 5 Drawing Sheets

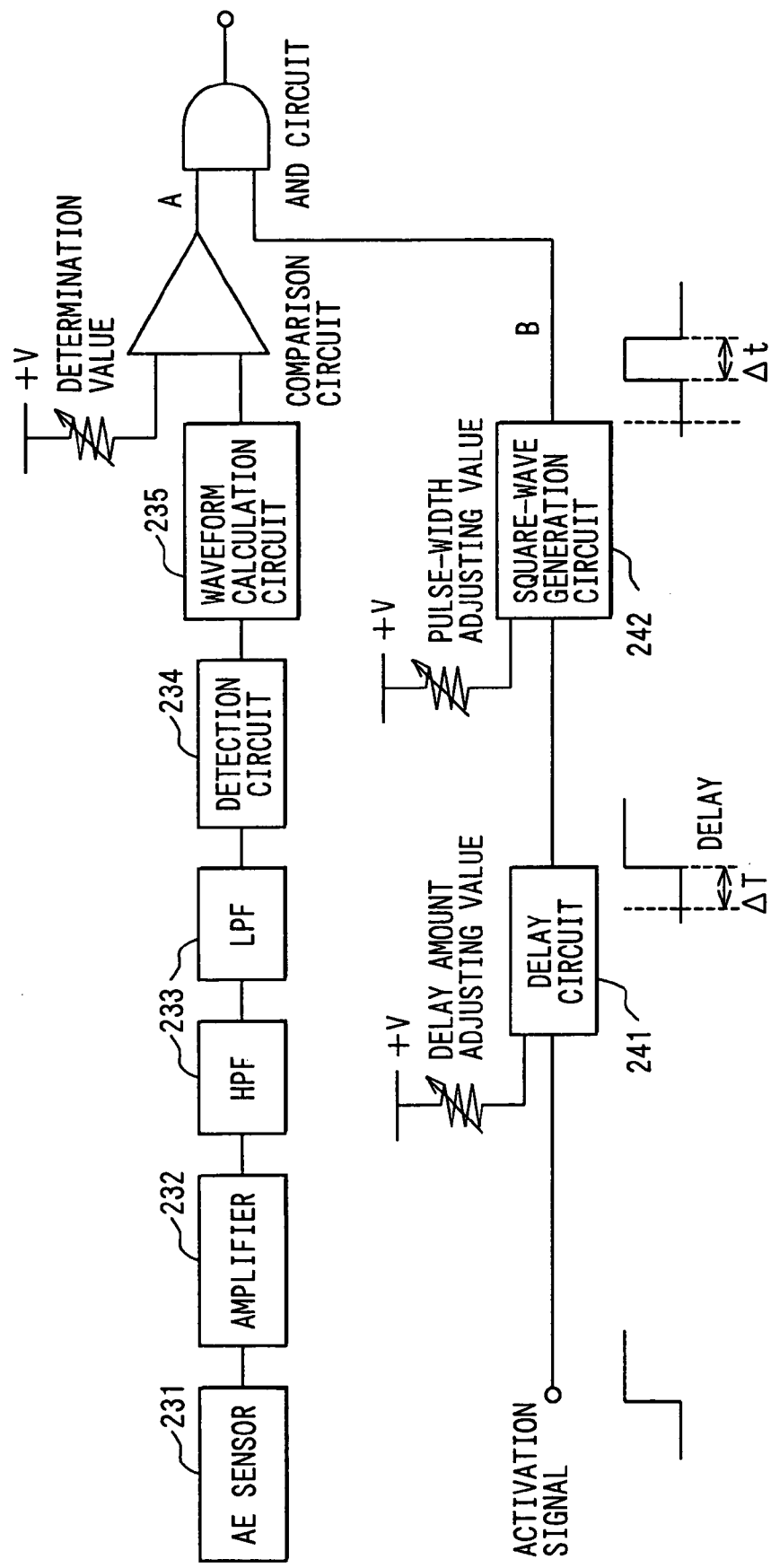

ABNORMALITY DETERMINATION AND ESTIMATION METHOD FOR PRODUCT OF PLASTIC WORKING, AND AN ABNORMALITY DETERMINATION AND ESTIMATION DEVICE

CROSS REFERENCE TO RELATED APPLICATION

This application is based upon, claims the benefit of priority of, and incorporates by reference Japanese Patent Application No. 2003-157002 filed Jun. 2, 2003.

BACKGROUND OF THE INVENTION

1. Field of the Invention

The present invention relates to an abnormality determination and estimation method and an abnormality determination and estimation device for products of plastic working. More particularly, the present invention relates to an abnormality determination and estimation method and an abnormality determination and estimation device that estimate discrimination of abnormalities based on an elastic wave generated in a plastic working process.

2. Description of the Related Art

Generally, a technique has been known that uses an AE sensor for detecting an elastic wave generated when a local deformation or destruction occurs prior to entire destruction of a structure so as to monitor the structure and/or predict the destruction of the structure. This technique is used for nondestructive inspection. Thus, the present invention employs this AE sensor in a plastic working apparatus and detects the elastic wave generated in the structure in the plastic working apparatus by means of the AE sensor and estimates the detected elastic wave with respect to an elastic wave in a case of forming a non-defective product. This estimates the presence of an abnormality of the parts formed by plastic working, and determines the abnormality.

However, in a case where a determination value for estimating an abnormality, which is used for comparing a defective product and a nondefective product, is set in such a manner that the comparison is done based on the magnitude of the amplitude of the elastic wave thus detected, it is difficult to determine the difference from the characteristic value because the amplitude of the elastic wave generated when a die hits something in the plastic working process is large. This may result in a wrong determination.

Therefore, the present invention was made considering the above drawback and aims to provide an abnormality determination and estimation method and an abnormality determination and estimation device for products of plastic working to improve the precision of detection of abnormalities and discriminate the abnormalities by estimating an elastic wave for each processing step.

SUMMARY OF THE INVENTION

In order to achieve the above object, the present invention employs technical means. The invention according to a first aspect is characterized such that an abnormality determination and estimation method for a product of plastic working includes an AE sensor (20), provided in a processing apparatus (10), for detecting an elastic wave in this processing apparatus (10) and an abnormality determination and estimation method (200a). The abnormality determination and estimation method (200a) is for discriminating at least two or more abnormalities of the product of plastic working and estimating the presence or absence of the abnormality for each processing step of the processing apparatus (10) based on the elastic wave detected by the AE sensor (20).

According to this aspect, abnormalities in plastic working can be determined and estimated by including the AE sensor (20) and the abnormality determination and estimation method (200a) for discriminating at least two or more abnormalities of the product of plastic working and estimating the presence or absence of the abnormality based on the elastic wave changing in each processing step of plastic working.

A second aspect of the invention is characterized in that the abnormality determination and estimation method (200a) estimates the presence or absence of the abnormality of the product of plastic working with respect to an elastic wave in processing of a non-defective product, based on a first elastic wave (A1). The first elastic wave is an elastic wave generated in a processing step immediately before an upper die comes into contact with a lower die after start of plastic working. A second elastic wave (A2), which is an elastic wave generated in a processing step when the upper die comes into contact with the lower die, and a third elastic wave (A3), which is an elastic wave generated in a processing step after the upper die comes into contact with the lower die, are also used in the estimation method.

According to a second aspect of the invention, the processing steps are specifically divided into at least three steps in this type of processing. By the abnormality determination and estimation method (200a), which estimates the elastic wave generated in each of the three steps with respect to the elastic wave in a case of processing of the non-defective product, a defect caused by the abnormality corresponding to each processing step can be estimated. Therefore, it is possible to improve precision of the abnormality detection and discriminate the abnormalities.

The invention has a third aspect such that plastic working is press working using the upper die and the lower die, the first elastic wave (A1) is an elastic wave for estimating an impact mark defect of a pressed product; the second elastic wave (A2) is an elastic wave for estimating a defect caused by a breakage of the die; and the third elastic wave (A3) is an elastic wave for estimating a defect caused by wear of the die. In general, major abnormalities in press working include the impact mark defect of a processed part caused by the entering of a foreign object, a breakage defect of the processed part caused by breakage of a punch of the die, and a wear defect such as a burr in the processed part, caused by wearing of the die. According to the invention of this third aspect, those abnormalities can be classified by processing steps, and discrimination of the abnormalities can be estimated.

The invention according to a fourth aspect is such that the impact mark defect of the pressed product is estimated by an integral value of the elastic wave generated in the processing step immediately before the upper die comes into contact with the lower die, as the first elastic wave (A1). Since the level of the elastic wave in that processing step is low, according to this fourth aspect, the precision of the abnormality detection can be improved by using the integral value of the elastic wave.

The invention according to a fifth aspect is characterized in that the defect caused by the breakage of the die is estimated by the maximum value of the elastic wave generated in the processing step when the upper die comes into contact with the lower die, as the second elastic wave (A2). Since the level of the elastic wave in that processing step is extremely high, according to this fifth aspect of the invention, the abnormality can be detected by using the maximum value of the elastic wave, without causing a wrong determination.

The invention according to a sixth aspect is such that the defect caused by the wear of the die is estimated by the integral value of the elastic wave generated in the processing step after the upper die comes into contact with the lower die, as the third elastic wave (A3). Since the level of the elastic wave in that processing step is low, according to this aspect of the invention, the precision of the abnormality detection can be improved by using the integral value of the elastic wave.

The invention according to a seventh aspect is such that an abnormality determination and estimation device for a product of plastic working in the plastic working, includes an AE sensor (20), provided in a processing apparatus (10), for detecting an elastic wave in this processing apparatus (10), and an abnormality determination and estimation means (200a) for discriminating at least two or more abnormalities and estimating the presence or absence of the abnormality of the product of plastic working based on the elastic wave detected by the AE sensor (20) for every processing step of the processing apparatus (10). According to the seventh aspect of the invention, the abnormalities in plastic working can be determined and estimated by including the AE sensor (20) and the abnormality determination and estimation means (200a) for discriminating at least two or more abnormalities of the product of plastic working and estimating the presence or absence of the abnormality based on the elastic wave changing in each processing step of plastic working.

The invention according to an eighth aspect is such that the abnormality determination and estimation device (200a) estimates the presence or absence of the abnormality of the product of plastic working based on a first elastic wave (A1), which is an elastic wave generated in a processing step immediately before an upper die comes into contact with a lower die after start of the plastic working, a second elastic wave (A2), which is an elastic wave generated in a processing step when the upper die comes into contact with the lower die, and a third elastic wave (A3), which is an elastic wave generated in a processing step after the upper die comes into contact with the lower die. According to this eighth aspect, the processing step can be divided into at least three steps in a case of this type of processing, when they are specifically divided, as in the second aspect. By the abnormality determination and estimation device (200a) that estimates the elastic wave in each of three steps, with respect to an elastic wave in a case of processing a non-defective product, a defect caused by the abnormality corresponding to each step can be estimated. Therefore, it is possible to improve precision of the abnormality detection and discriminate the abnormalities.

The invention according to a ninth aspect is characterized in that the plastic working is press working using the upper die and the lower die, the first elastic wave (A1) is an elastic wave for estimating an impact mark defect of a pressed product, the second elastic wave (A2) is an elastic wave for estimating a defect caused by a breakage of the die, while the third elastic wave (A3) is an elastic wave for estimating a defect caused by the wear of the die.

In the press working, in general, major abnormalities include the impact mark defect of the processed part because of entering of a foreign object, the breakage defect of the processed part caused by the breakage of the punch of the die and the defect caused by the wear of the die, such as a burr in the processed part. According to the invention of the ninth aspect, like the third aspect, those abnormalities are classified by the steps and thus, discrimination of the abnormalities can be estimated.

The invention according to a tenth aspect is such that the impact mark defect of the pressed product is estimated by an integral value of the elastic wave generated in the processing step immediately before the upper die comes into contact with the lower die, as the first elastic wave (A1). Since the level of the elastic wave in that processing step is low, according to this tenth aspect, the precision of the abnormality detection can be improved by using the integral value of the elastic wave.

The invention according to an eleventh aspect is such that the defect caused by the breakage of the die is estimated by the maximum value of the elastic wave generated in the processing step when the upper die comes into contact with the lower die, as the second elastic wave (A2). Since the level of the elastic wave in that processing step is extremely high, according to the eleventh aspect of the invention, the abnormality can be detected by using the maximum value of the elastic wave, without causing a wrong determination.

The invention according to a twelfth aspect is such that the defect caused by the wear of the die is estimated by the integral value of the elastic wave generated in the processing step after the upper die comes into contact with the lower die, as the third elastic wave (A3). Since the level of the elastic wave in that processing step is low, according to this twelfth aspect, the precision of the abnormality detection can be improved by using the integral value of the elastic wave.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 5 is a block diagram showing an abnormality determination and estimation method according to one embodiment of the present invention.

DETAILED DESCRIPTION OF THE PREFERRED EMBODIMENTS

The following description of the preferred embodiments is merely exemplary in nature and is in no way intended to limit the invention, its application, or uses.

Figure 1:
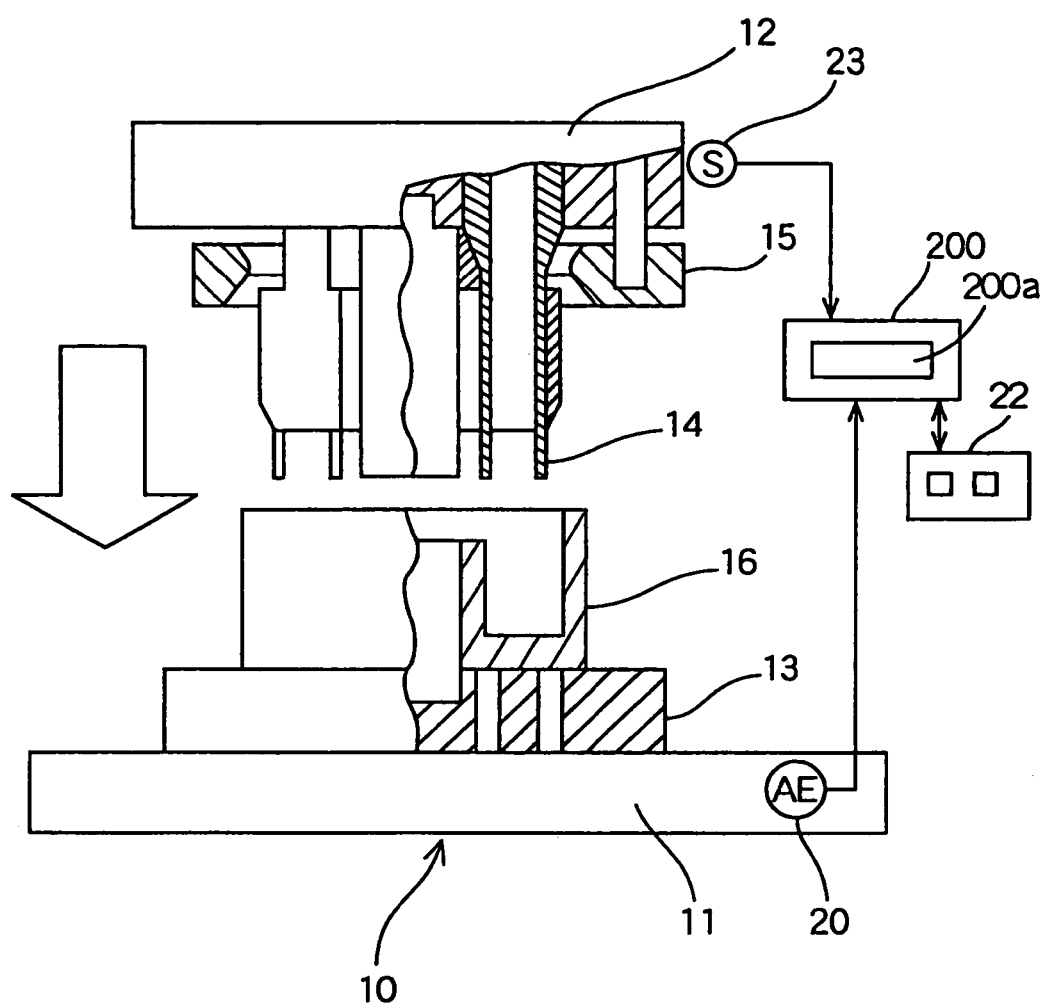
FIG. 1 is a schematic diagram of a general structure of an abnormality determination and estimation device for a pressed product according to one embodiment of the present invention.

An abnormality determination and estimation device for pressed products in press working will be described below, with reference to FIGS. 1 through 5. FIG. 1 is a schematic diagram of a general structure of a pressing apparatus 10 as a processing apparatus, to which an abnormality determination and estimation device for products of plastic working is applied. The abnormality determination and estimation device of the present embodiment includes the pressing apparatus 10, an AE sensor 20 for detecting an elastic wave, and a controlling unit 200 for controlling abnormality determination.

In the pressing apparatus 10, a die for processing a work piece 16 as a processed part by plastic working is secured. The die is divided into an upper die 12 and a die set 13 as a lower die that is secured on a press bed 11 in the pressing apparatus 10. The upper die 12 is provided with a punch 14 used for plastic working of the work piece 16 and a stripper 15 for holding the work piece 16. While the work piece 16 as the processed part is placed on the die set 13, the upper die 12 is moved from a top dead center position to a bottom dead center position by crank driving, thereby the workpiece 16 is processed by plastic working.

An operating panel 22 for operating the pressing apparatus 10 is provided, and a start/stop switch and display means such as indicator lights for displaying details of abnormalities are also provided although they are not shown. Operation signals from them are input to a controlling unit 200. The AE sensor 20 is a sensor for detecting an elastic wave generated by release of strain energy that occurs when deformation, a crack, or destruction occurs in solid material because of stress. The AE sensor 20 is provided on the press bed 11.

This elastic wave is also called as acoustic emission. The AE sensor 20 is configured to input the detected elastic wave to the controlling unit 200. Moreover, a position sensor 23 detects a crank angle during the movement of the upper die 12 from the top dead center position to the bottom dead center position by crank driving. The position sensor 23 is configured to input position information, such as the crank angle thus detected, to the controlling unit 200.

The controlling unit 200 is formed mainly by a microcomputer, and includes abnormality determination and estimation means 200a, that is an abnormality determination and estimation method, as a control program for discriminating and estimating the presence of abnormalities in the processed part in a built-in ROM (not shown). This control program is a program for discriminating and estimating the presence or absence of the processed part based on the elastic wave detected by the AE sensor 20, and, in a case where there is any abnormality, discriminating the detail of the abnormality, notifying that, and stopping the processing apparatus 10.

Therefore, the controlling unit 200 of the present embodiment is configured in such a manner that an elastic-wave detection signal from the AE sensor 20, the position information from the position sensor 23, and the operation signals from the operation panel 22 are input to the controlling unit 200 while the controlling unit 200 issues a notification to the operation panel 22 and outputs a stop signal. The position information input from the position sensor 23 causes output of an ON signal as an activation signal that is output to the abnormality determination and estimation means 200a and indicates that the processing apparatus 10 is being driven when the crank angle is in a range of 170°–190°, and causes output of an OFF signal as the activation signal when the crank angle is out of the range of 170°–190°.

Figure 2:
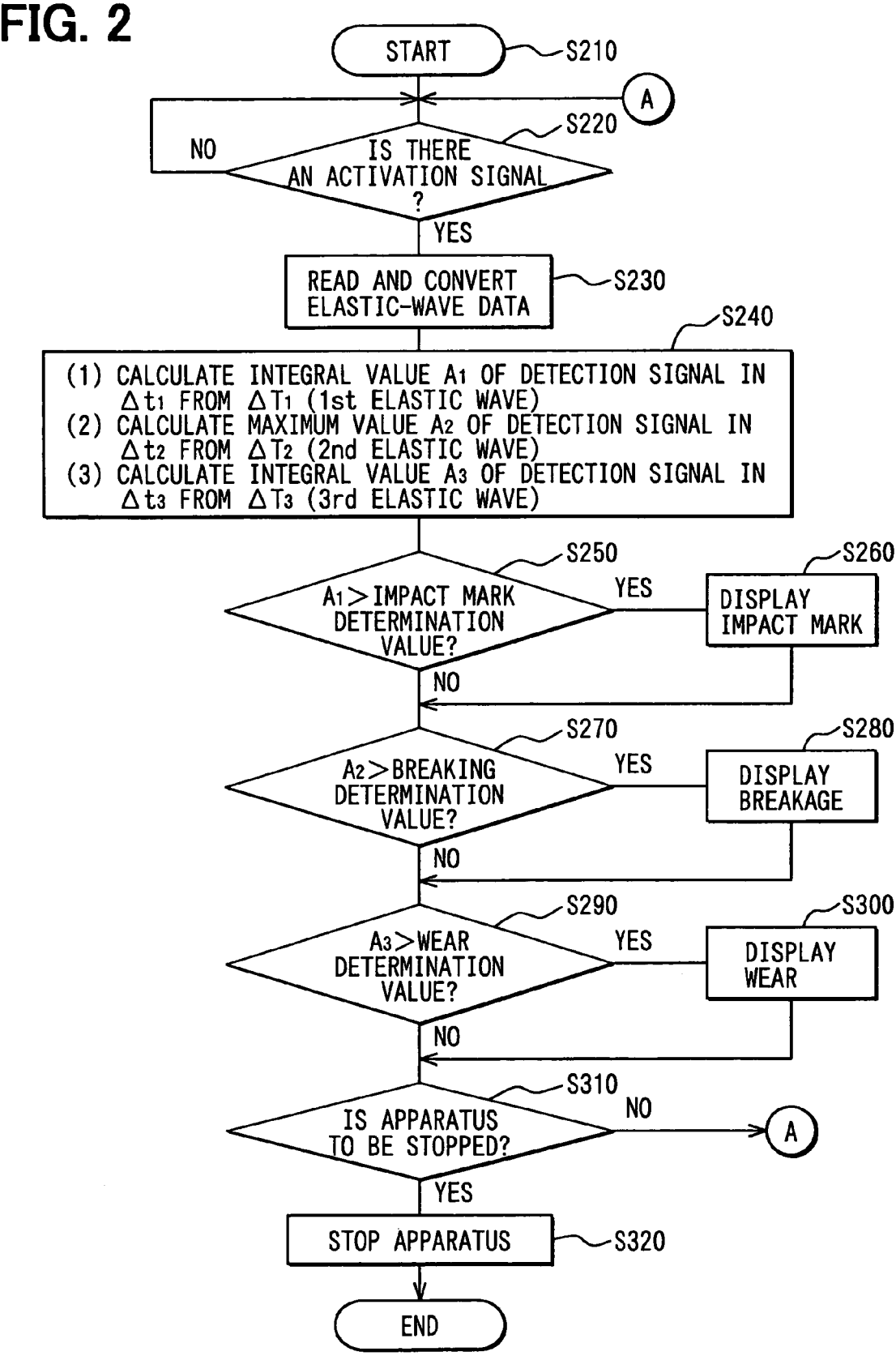
FIG. 2 is a flowchart of a control procedure by an abnormality determination and estimation means according to one embodiment of the present invention.

An operation of the abnormality determination and estimation device for pressed products having the above structure is described based on a flowchart of the abnormality determination and estimation means 200a shown in FIG. 2. First, as shown in FIG. 2, when the work piece 16 is placed on the die set 13 and the start switch (not shown) is turned ON, a main routine of a control procedure starts and initialization of stored contents in a data-processing memory (RAM) and the like is performed (step S210).

In step S220, it is determined whether or not the activation signal exists. In other words, it is determined whether or not the activation signal is an ON signal indicating that the crank angle, resulting from the detection of the driven position of the upper die 12 by the position sensor 23, is in the range of 170°–190°. This angle is the position of the upper die 12 from a time immediately before the upper die 12 comes into contact with the die set 13 to a time immediately after they come into contact with each other, which is detected as the ON signal.

When the activation signal was ON in step S220, the procedure goes to step S230 where the elastic wave input from the AE sensor 20 is read and is subjected to data conversion. Then, in step S240, the elastic wave after data conversion is calculated. In the present embodiment, in order to estimate at least three abnormalities in respective steps of the pressing process, the elastic wave is calculated in separate manners.

More specifically, the first elastic wave A1 generated in a step of the pressing process, immediately before the upper die 12 comes into contact with the lower die 13, the second elastic wave A2 generated in a step of the pressing process when the upper die 12 comes into contact with the lower die 13, and the third elastic wave A3 generated in a step of the pressing process immediately after the upper die 12 comes into contact with the lower die 13, are calculated separately. This is because abnormalities of the processed part (work piece 16) in press working are classified into abnormalities caused by at least three defects. For example, the defects include an impact mark defect in which an impact mark remains in the work piece 16 when the dies sandwich a foreign object such as a piece, between the dies, a breakage defect caused by a breakage of the die such as the punch 14 or die set 13, and a wear defect such as a burr occurring in the work piece 16 because of degradation and wear of the die such as the punch 14 or the die set 13.

Figure 3:
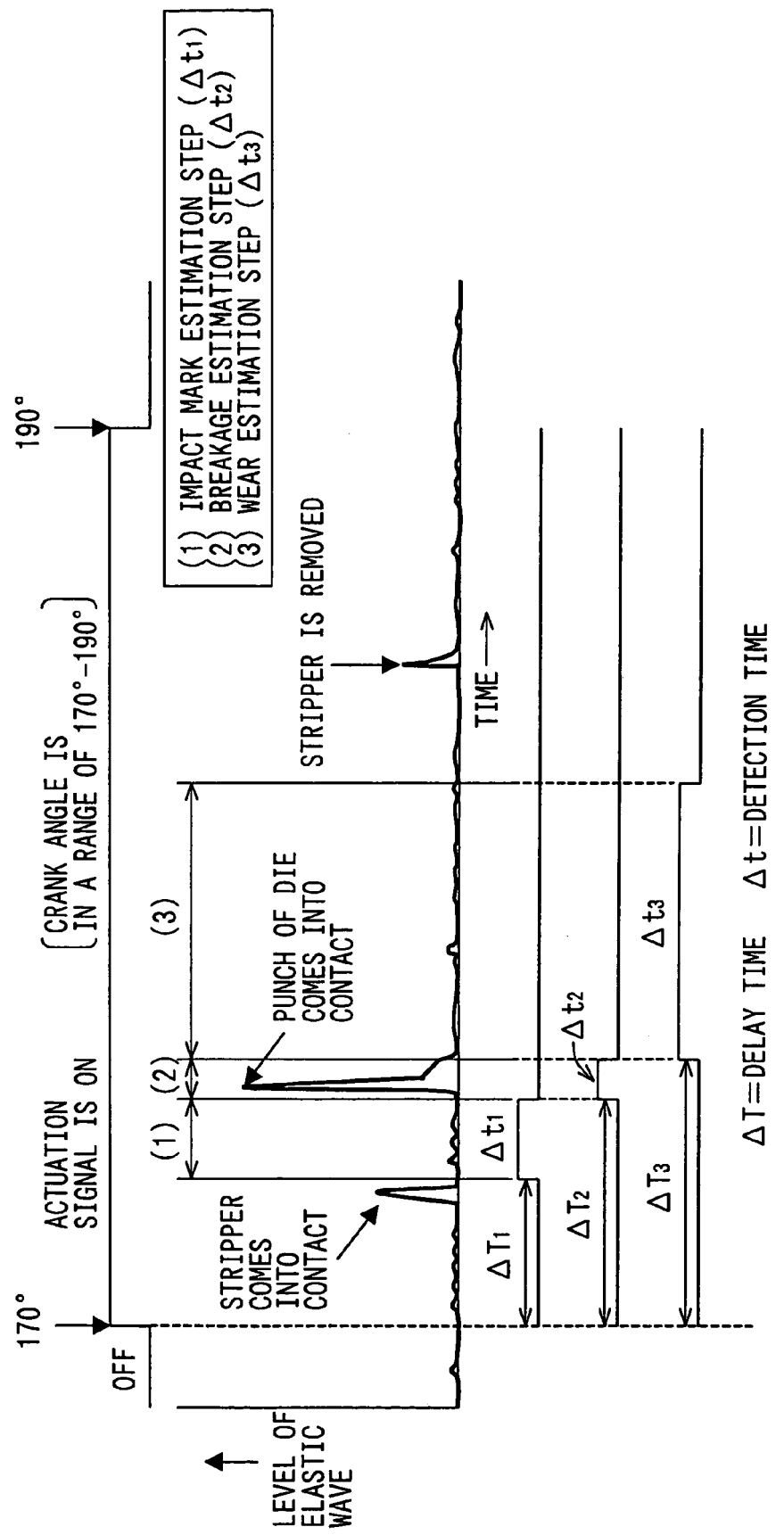
FIG. 3 is a characteristic diagram of a relationship between a level of an elastic wave and time according to one embodiment of the present invention.

Therefore, in the present embodiment, a period in which the activation signal is ON, i.e., a period in the processing step in which the crank angle detected by the position sensor 23 is in the range of 170°–190° is divided into at least three, as shown in FIG. 3, the calculation of the elastic wave is done for each of those steps. FIG. 3 is a characteristic diagram of a relationship between the level of the elastic wave and the time while the activation signal is ON. In press working, the amplitude of the elastic wave becomes large when the stripper 15 of the die comes into contact with the lower die 13, when the punch 14 comes into contact with the work piece 16, and when the stripper 15 is removed from the lower die 13.

Thus, in the present embodiment, the steps for calculating the elastic wave are set to include steps (1) to (3), i.e., a step at which the punch 14 comes into contact with the work piece 16, and steps before and after those steps. Step (1) in FIG. 3 is an impact-mark defect estimation step immediately before the aforementioned upper die 12 comes into contact with the lower die 13. In this step, the impact-mark defect of the abnormalities is estimated based on the first elastic wave A1.

Step (2) in FIG. 3 is a breakage defect estimation step for estimating the breakage defect when the upper die 12 comes into contact with the lower die 13. In this step, the breakage defect of the abnormalities is estimated based on the second elastic wave A2. Step (3) in FIG. 3 is a wear defect estimation step immediately after the upper die 12 comes into contact with the lower die 13. In this step, the wear defect of the abnormalities is estimated based on the third elastic wave A3. In FIG. 3, ΔT is a delay time after the activation signal turns ON, while Δt is a detection time in which the elastic wave is detected.

The breakage defect may occur in the estimation step (3). This occurs in a case where a damage or breakage occurs in the punch or die set immediately after the upper die comes into contact with the lower die. Whether the breakage defect occurs in the processing step (2) or in the processing step (3), the abnormalities can be discriminated as long as the elastic wave generated in the processing step (3) contains both the elastic wave caused by the product in a case of breakage and the elastic wave caused by the product in a case of wear or contains the latter elastic wave only. Therefore, only by performing the estimation steps (1) and (3), it is possible to estimate and detect the defective products.

Figure 4:
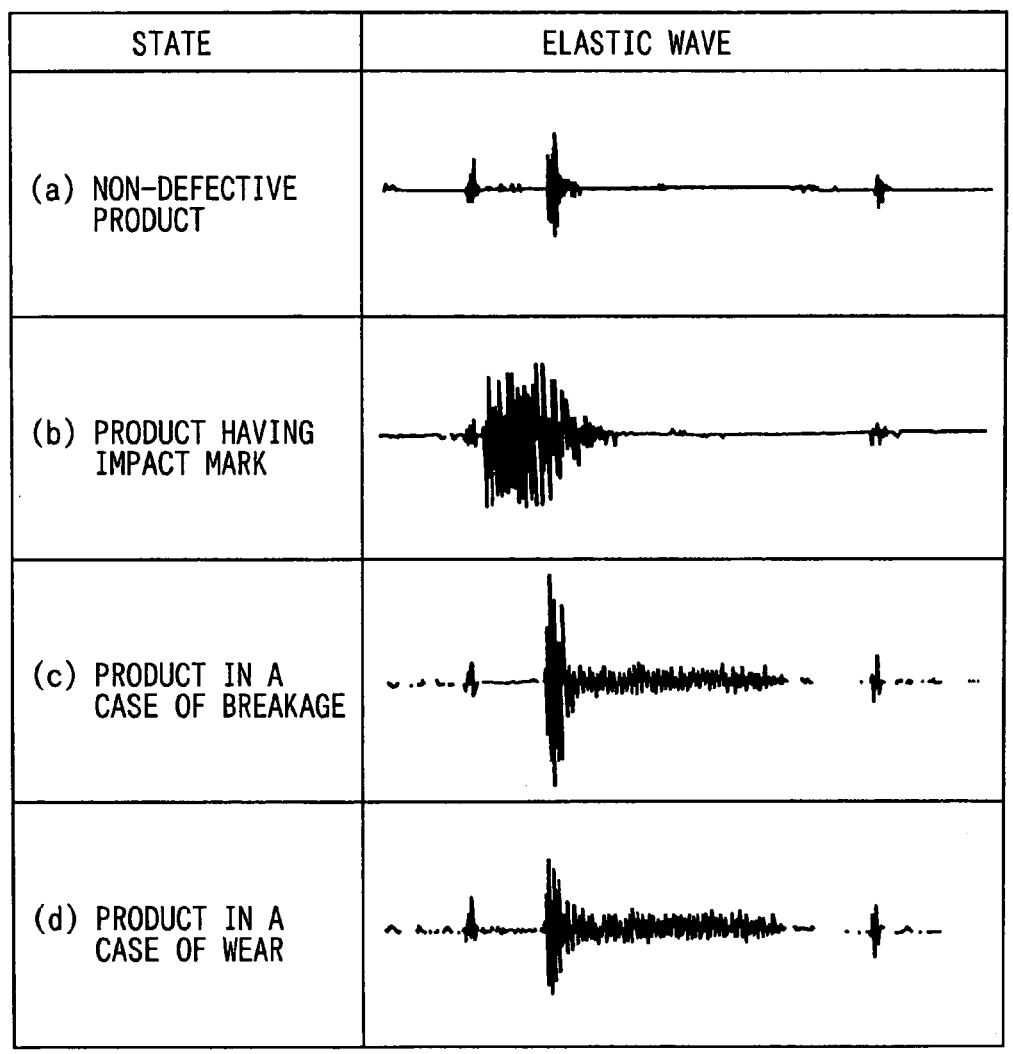
FIG. 4 is a characteristic diagram of a relationship between abnormality modes and the elastic wave according to one embodiment of the present invention.

Next, the basis of the estimation in the above-described manner, made clear by some experiments conducted by the inventors, is described with reference to FIG. 4. FIG. 4 shows the elastic wave detected in every abnormality mode while the activation signal is ON; (a) shows the elastic wave generated in a case of press working a non-defective product; (b) shows the elastic wave generated in a case of processing a product having an impact mark; (c) shows the elastic wave in a case of processing with the punch 14 that is broken; (d) shows the elastic wave in a case of processing a product with the worn die.

When the elastic waves in (b) to (d) are compared with the elastic wave of the non-defective product (a), the elastic wave that is not generated in the non-defective product is generated in the impact mark product (b) immediately before the dies come into contact with each other. The elastic wave has a drastic and large amplitude generated in the product in a case of breakage (c) and the amplitude of the elastic wave becomes larger in the product in a case of the worn die (d) than in the non-defective product (a) just when and immediately after the dies come into contact with each other. Therefore, the abnormality modes have a correlation with detection timings, as described above.

Moreover, in order to estimate the aforementioned abnormality modes precisely, in step S240, an integral value in the detection time Δt1 and that in the detection time Δt3 are calculated as the first elastic wave A1 and the third elastic wave A3, and the maximum value in the detection time Δt2 is calculated as the second elastic wave A2. The reason for this is as follows. In the impact mark defect estimation step (1) and the wear defect estimation step (3), the amplitude of the elastic wave is relatively small. Therefore, in order to improve the precision of abnormality detection, the integral value is used. In the breakage defect estimation step (2), the amplitude of the elastic wave becomes extremely large when the abnormality occurs than that when the punch 14 of the die comes into contact with the work piece. Therefore, the maximum value is used as the second elastic wave A2.

From the above consideration, in step S240, as the first elastic wave A1, the integral value of the detection signal is calculated from the AE sensor 20 in the detection time Δt1 after the delay time ΔT1 has passed after the input of the activation signal. Similarly, the second and third elastic waves A2 and A3 are calculated. Then, in step S250, abnormality estimation is done by comparing the thus calculated first elastic wave A1 with an impact mark determination value.

In other words, it is determined whether or not the first elastic wave A1 is larger than the impact mark determination value. If YES, a notification of an impact mark abnormality mode is output in step S260. If NO, abnormal estimation is done by comparing the thus calculated second elastic wave A2 with a breakage determination value in step S270. In this estimation, it is determined whether or not the second elastic wave A2 is larger than the breakage determination value like the estimation of the impact mark abnormality.

If YES, a notification of a breakage abnormality mode is output in step 280. If NO, abnormality estimation is done by comparing the thus calculated third elastic wave A3 with a wear determination value. That is, it is determined whether or not the third elastic wave A3 is larger than the wear determination value. If YES, notification of a wear abnormality mode is output in step S300.

If NO, it is determined in step S310 whether or not the processing apparatus 10 is to be stopped. In this embodiment, since the processing apparatus 10 is stopped if any one of the aforementioned three abnormalities is found, a stop signal for stopping the processing apparatus 10 is output in step S320. Thus, the processing apparatus 10 is stopped and the abnormality mode thus found is displayed.

In the present embodiment, the flowchart shown in FIG. 2 is used for estimating discrimination of the abnormalities in press working. However, instead of that flowchart, an estimation method for determining and estimating abnormalities by a block diagram may be used, as shown in FIG. 5. This block diagram is explained below. Elastic wave data detected by the AE sensor 20 (step S231) is amplified by an amplifier (step S232). Then, noises in a high-frequency region and a low-frequency region are removed by an HPF (high-pass filter) and an LPF (low-pass filter) (step S233) and thereafter a detection circuit detects the elastic wave data (step S234).

Then, a waveform calculation circuit (step S235) calculates the amplitude and energy of the elastic wave based on the thus detected waveform and thereafter a comparison circuit (step S236) compares the calculation result with a determination value. When the calculation result exceeds the determination value, an AND circuit (step S236) next to the comparison circuit outputs an abnormal signal A. On the other hand, based on the activation signal, a square-wave generation circuit (step S242) works after a delay time AT that was preset in a delay circuit (step S241) where a timer is counted, for example.

The square-wave generation circuit (step S242) outputs a signal B causing generation of a pulse during a period corresponding to the detection time Δt in which the elastic wave is detected. In this period, the abnormal signal A is also output. Therefore, by setting a plurality of delay times ΔT and detection times Δt that correspond to a plurality of abnormality modes, for example, the impact mark defect, the breakage defect, and the wear defect as in the present embodiment, respectively, the abnormalities can be discriminated and recognized. In the above description, the wear defect may include excessively large or small clearance of the dies, lack of oil for processing, a change in dimensions of the work piece 16, and a crack or breakage of the work piece 16, other than a burr.

According to the aforementioned abnormality determination and estimation device in press working of one embodiment of the present invention, the pressing process can be divided into at least three steps in a case of plastic working, such as this type of press working. More specifically, the abnormality determination and estimation device includes the abnormality determination and estimation means 200a that estimates the presence or absence of abnormality of a product of plastic working with respect to the elastic wave in a case of processing a non-defective product, based on the first elastic wave A1 that is an elastic wave generated in the processing step immediately before the upper die comes into contact with the lower die, the second elastic wave A2 that is an elastic wave generated in the processing step when the upper die comes into contact with the lower die, and the third elastic wave A3 that is an elastic wave generated in the processing step after the upper die comes into contact with the lower die. This makes it possible to estimate defects caused by the abnormalities corresponding to the respective steps. Thus, it is possible to improve the precision of the abnormality detection and discriminate the abnormalities.

In press working, in general, major abnormalities are an impact mark defect in which an impact mark remains in the processed part because of the entrance of a foreign object, a breakage defect caused by any breakage of the punch of the die, and a wear defect such as a burr, caused by the wear of the die. These abnormalities are classified by the aforementioned three processing steps, thereby the discrimination of the abnormalities can be estimated.

The impact mark defect of the pressed product is estimated by the integral value of the elastic wave generated in the processing step immediately before the upper die comes into contact with the lower die. Thus, since the level of the elastic wave in that processing step is low, the first elastic wave A1 is obtained as the integral value of the elastic wave. Therefore, the precision of the abnormality detection can be improved.

The breakage defect caused by the breakage of the die is estimated by the maximum value of the elastic wave generated in the processing step when the upper die comes into contact with the lower die. Thus, since the level of the elastic wave in that processing step is extremely high, the second elastic wave A2 is obtained as the maximum value of the elastic wave. Therefore, the abnormality can be detected without causing a wrong determination.

The wear defect caused by the wear of the die is estimated by the integral value of the elastic wave generated in the processing step after the upper die comes into contact with the lower die. Thus, since the level of the elastic wave in that processing step is low, the third elastic wave A3 is obtained as the integral value of the elastic wave. Therefore, the precision of the abnormality detection can be improved.

Another Embodiment

Although the processing process is divided into three steps and the elastic wave is detected in each step in the above embodiment, the number of divisions is not limited thereto. The process may be divided into two or more steps.

Although the AE sensor 20 is provided on the press bed 11 in the above embodiment, the arrangement of the AE sensor 20 is not limited thereto. The AE sensor 20 may be provided in the lower die. Moreover, although the present invention is applied to press working in the above embodiment, the present invention can be applied to various types of plastic working other than press working.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An abnormality determination and estimation method for a product of plastic working, comprising:
   providing an AE sensor in a processing apparatus of the product of the plastic working, for detecting an elastic wave in the processing apparatus; and
   performing an abnormality determination and estimation for discriminating at least two or more abnormalities of the product of plastic working and estimating a presence or an absence of the abnormality for each processing step of the processing apparatus based on the elastic wave that is generated in the processing step of the plastic working detected by the AE sensor; wherein
   performing the abnormality determination and estimation step estimates the presence or absence of the abnormality of the product of plastic working with respect to an elastic wave in processing of a non-defective product, based on a first elastic wave that is an elastic wave generated in a processing step immediately before an upper die comes into contact with a lower die after start of plastic working, a second elastic wave that is an elastic wave generated in a processing step when the upper die comes into contact with the lower die, and a third elastic wave that is an elastic wave generated in a processing step after the upper die comes into contact with the lower die.

2. The abnormality determination and estimation method for a product of plastic working according to claim 1, wherein
   the plastic working is press working using the upper die and the lower die, the first elastic wave is an elastic wave for estimating an impact mark defect of a pressed product,
   the second elastic wave is an elastic wave for estimating a defect caused by a breakage of the die,
   and the third elastic wave is an elastic wave for estimating a defect caused by wear and the die.

3. The abnormality determination and estimation method for a product of plastic working according to claim 2, wherein
   the impact mark defect of the pressed product is estimated by an integral value of the elastic wave generated in the processing step immediately before the upper die comes into contact with the lower die as the first elastic wave.

4. The abnormality determination and estimation method for a product of plastic working according to claim 2, wherein
   the defect caused by the breakage of the die is estimated by the maximum value of the elastic wave generated in the processing step when the upper die comes into contact with the lower die as the second elastic wave.

5. The abnormality determination and estimation method for a product of plastic working according to claim 2, wherein
   the defect caused by the wear of the die is estimated by the integral value of the elastic wave generated in the processing step after the upper die comes into contact with the lower die as the third elastic wave.

6. An abnormality determination and estimation device for a product of plastic working in the plastic working, comprising:
   an AE sensor, provided in a processing apparatus of the product of the plastic working, for detecting an elastic wave in the processing apparatus; and
   abnormality determination and estimation means for discriminating at least two or more abnormalities and estimating a presence or absence of the abnormality of the product of plastic working based on the elastic wave that is generated in the plastic working detected by the AE sensor for every processing step of the processing apparatus; wherein the abnormality determination and estimation device estimates the presence or absence of the abnormality of the product of plastic working based on a first elastic wave that is an elastic wave generated in a processing step immediately before an upper die comes into contact with a lower die after start of the plastic working, a second elastic wave that is an elastic wave generated in a processing step when the upper die comes into contact with the lower die, and a third elastic wave that is an elastic wave generated in a processing step after the upper die comes into contact with the lower die.

7. The abnormality determination and estimation device for a product of plastic working according to claim 6, wherein the plastic working is press working using the upper die and the lower die, the first elastic wave is an elastic wave for estimating an impact mark defect of a pressed product, the second elastic wave is an elastic wave for estimating a defect caused by a breakage of the die, and the third elastic wave is an elastic wave for estimating a defect caused by the wear of the die.

8. The abnormality determination and estimation device for a product of plastic working according to claim 7, wherein the impact mark defect of the pressed product is estimated by an integral value of the elastic wave generated in the processing step immediately before the upper die comes into contact with the lower die as the first elastic wave.

9. The abnormality determination and estimation device for a product of plastic working according to claim 7, wherein the defect caused by the breakage of the die is estimated by the maximum value of the elastic wave generated in the processing step when the upper die comes into contact with the lower die as the second elastic wave.

10. The abnormality determination and estimation device for a product of plastic working according to claim 7, wherein the defect caused by the wear of the die is estimated by the integral value of the elastic wave generated in the processing step after the upper die comes into contact with the lower die as the third elastic wave.

11. An abnormality determination and estimation method for a product of plastic working, comprising:

providing an AE sensor in a processing apparatus of the product of the plastic working;

detecting an elastic wave that is generated during a processing step of the plastic working in the processing apparatus, with the AE sensor:

discriminating at least two or more abnormalities of the product of the plastic working;

estimating a presence or absence of the abnormality for each processing step of the processing apparatus during the plastic working, based on the elastic wave detected by the AE sensor; and estimating the presence or absence of the abnormality of the product of plastic working with respect to an elastic wave in processing of a non-defective product, based on a first elastic wave that is an elastic wave generated in a processing step immediately before an upper die comes into contact with a lower die after start of plastic working, a second elastic wave that is an elastic wave generated in a processing step when the upper die comes into contact with the lower die, and a third elastic wave that is an elastic wave generated in a processing step after the upper die comes into contact with the lower die.

12. The abnormality determination and estimation method for a product of plastic working according to claim 11, wherein the plastic working is press working using the upper die and the lower die, the first elastic wave is an elastic wave for estimating an impact mark defect of a pressed product, the second elastic wave is an elastic wave for estimating a defect caused by breakage of the die, and the third elastic wave is an elastic wave for estimating a defect caused by wear of the die.

13. The abnormality determination and estimation method for a product of plastic working according to claim 12, wherein the impact mark defect of the pressed product is estimated by an integral value of the elastic wave generated in the processing step immediately before the upper die comes into contact with the lower die, as the first elastic wave.

14. The abnormality determination and estimation method for a product of plastic working according to claim 12, wherein the defect caused by the breakage of the die is estimated by the maximum value of the elastic wave generated in the processing step when the upper die comes into contact with the lower die, as the second elastic wave.

15. The abnormality determination and estimation method for a product of plastic working according to claim 12, wherein the defect caused by the wear of the die is estimated by the integral value of the elastic wave generated in the processing step after the upper die comes into contact with the lower die, as the third elastic wave.

16. An abnormality determination and estimation method for a product of plastic working, comprising:

providing an AE sensor in a processing apparatus of the product of the plastic working, for detecting an elastic wave in the processing apparatus; and performing an abnormality determination and estimation for discriminating at least two or more abnormalities of the product of plastic working and estimating a presence or an absence of the abnormality for each processing step of the processing apparatus based on the elastic wave that is generated in the processing step of the plastic working detected by the AE sensor; wherein the abnormality determination and estimation step estimates the presence or absence of the abnormality for each processing step of the processing apparatus based on at least first and second elastic waves detected by the AE sensor;

the first elastic wave is generated in a processing step when a pair of opposite dies used for the plastic working are positioned at a first position; and the second elastic wave is generated in a processing step when the pair of opposite dies used for the plastic working are positioned at a second position different from the first position.

17. An abnormality determination and estimation device for a product of plastic working in the plastic working, comprising:

an AE sensor, provided in a processing apparatus of the product of the plastic working, for detecting an elastic wave in the processing apparatus; and abnormality determination and estimation means for discriminating at least two or more abnormalities and estimating a presence or absence of the abnormality of the product of plastic working based on the elastic wave that is generated in the plastic working detected by the AE sensor for every processing step of the processing apparatus; wherein the abnormality determination and estimation step estimates the presence or absence of the abnormality for each processing step of the processing apparatus based on at least first and second elastic waves detected by the AE sensor;

the first elastic wave is generated in a processing step when a pair of opposite dies used for the plastic working are positioned at a first position; and the second elastic wave is generated in a processing step when the pair of opposite dies used for the plastic working are positioned at a second position different from the first position.

18. An abnormality determination and estimation method for a product of plastic working, comprising:

providing an AE sensor in a processing apparatus of the product of the plastic working;

detecting an elastic wave that is generated during a processing step of the plastic working in the processing apparatus, with the AE sensor;

discriminating at least two or more abnormalities of the product of the plastic working;

estimating a presence or absence of the abnormality for each processing step of the processing apparatus during the plastic working, based on the elastic wave detected by the AE sensor; wherein the abnormality determination and estimation step estimates the presence or absence of the abnormality for each processing step of the processing apparatus based on at least first and second elastic waves detected by the AE sensor;

the first elastic wave is generated in a processing step when a pair of opposite dies used for the plastic working are positioned at a first position; and the second elastic wave is generated in a processing step when the pair of opposite dies used for the plastic working are positioned at a second position different from the first position.

* * * * *